United States Patent [19]

Folkers et al.

[11] 3,974,135

[45] Aug. 10, 1976

[54] SYNTHETIC DECAPEPTIDE HAVING THE ACTIVITY OF THE LUTEINIZING HORMONE RELEASING HORMONE AND METHOD FOR PRODUCING THE SAME

[76] Inventors: Karl Folkers, 6406 Mesa Drive, Austin, Tex. 78731; Hans Sievertsson, Organiska Avdelingen, Farmacheutiska Fakulteten, Uppsala Universitet, Box 6804, 113 86 Stockholm, Sweden

[22] Filed: June 8, 1972

[21] Appl. No.: 261,007

Related U.S. Application Data

[63] Continuation-in-part of Ser. No. 156,520, June 24, 1971, abandoned.

[52] U.S. Cl. .................. 260/112.5 LH; 424/177
[51] Int. Cl.$^2$.................. C07C 103/52; C07G 7/00
[58] Field of Search ................ 260/112.5, 112.5 CH

[56] References Cited
OTHER PUBLICATIONS

Matsuo et al., Biochem. Biophys. Res. Comm., 43, 1334 (1971).

Primary Examiner—Lewis Gotts
Assistant Examiner—Suyat Reginald J.
Attorney, Agent, or Firm—Salvatore C. Mitri

[57] ABSTRACT

A synthetic decapeptide, L-pglutamyl-L-histidyl-L-tryptophanyl-L-seryl-L-tyrosyl-glycyl-L-leucyl-L-arginyl-L-prolyl-glycinamide having the hormonal activity of the luteinizing hormone releasing hormone (LRH) of the hypothalamus gland of mammals is provided by utilizing, as key starting materials, the amino acids, pyroglutamic acid, histidine, tryptophan, serine, tyrosine, glycine, leucine, arginine, proline. Synthesis of the decapeptide is accomplished by coupling, in appropriate protected forms, all of the remaining amino acids, individually or in combination, to the starting amino acid, or amino acid group or to the terminal amino acid resulting from combinations with one or more other amino acids, bound to a resin or carrier followed by release of the decapeptide from the carrier as the amide or other form which is converted to the amide, L-pglutamyl-L-histidyl-L-tryptophanyl-L-seryl-L-tyrosyl-glycyl-L-leucyl-L-arginyl-L-prolyl-glycinamide.

2 Claims, No Drawings

SYNTHETIC DECAPEPTIDE HAVING THE ACTIVITY OF THE LUTEINIZING HORMONE RELEASING HORMONE AND METHOD FOR PRODUCING THE SAME

This is a continuation-in-part application of co-pending application Serial No. 156,520 filed June 24, 1971 now abandoned.

This invention relates to the decapeptide, L-pglutamyl-L-histidyl-L-tryptophanyl-L-seryl-L-tyrosyl-glycyl-L-leucyl-L-arginyl-L-prolyl-glycinamide, which is referred to hereinafter as "decapeptide-$NH_2$," and to methods for its synthesis. This synthetic decapeptide, decapeptide-$NH_2$, exhibits the same biological and hormonal activities as does the naturally occurring luteinizing hormone releasing hormone of the hypothalamus in the brain of mammels including man, this hormone being referred to hereinafter as "LRH".

BACKGROUND OF THE INVENTION

The luteinizing hormone releasing hormone (LRH) is well recognized to be one of the six or seven or more neurohormones of the hypothalamus of mammalian species, including man. The hypothalamus is a part of the forebrain Prosencephalon which, unlike the cerebellum and the cerebral hemispheres, has maintained, throughout its phylogenetic history, a relative constancy of arrangement. Basically, the hypothalamus is divisible into medial and lateral portions. The medial division joins the third ventricle. The lateral portion of the hypothalamus contains cells that are diffusely arranged among the fibers of what has long been called the medial forebrain bundle. An anatomic relationship which is a constant feature of the hypothalamus is its intimate association with the pituitary gland. The pituitary gland consists of the posterior and anterior lobes. Biochemical transport of the neurohormones of the hypothalamus to the anterior lobe is provided by certain blood vessels in a portal system which is a network of capillaries. The blood of these capillaries passes down the pituitary stalk and becomes distributed through another system of capillaries in the anterior lobe and one of the neurohormones thus transported is LRH.

In addition to LRH, there is a follicle stimulating hormone releasing hormone (FRH) and a prolactin releasing hormone (PRH). It is generally considered that there is one hypothalamic releasing hormone for each of the pituitary hormones of the anterior lobe, but this concept has not yet been proven. However, it has been established that there is a hypothalamic neurohormone which releases the luteinizing hormone of the anterior pituitary; that is, LRH. It appears that LRH also releases FSH, at least to some extent.

Presently, LRH is extracted from animal hypothalamic tissue obtained from many thousands of animals at slaughter houses with great difficulty since the size of the hypothalamic tissue from a full grown pig is only about 150 mg. The enormous task involved in obtaining pure LRH from animal tissue is exemplified by the fact that less than 0.5 mg. of purified, but not completely pure, LRH was obtained from the combined tissue of about 80,000 sheep. (Guillemin, *International Journal of Fertility*, Vol. 12, No. 4 pp. 359 (1967).) Guillemin stated that "the difficulties involved in the isolation of LRH are such, however, that we must consider as absolutely out of the question the use of hypothalamic hormones of natural sources for our clinical studies." It can be seen, therefore, that scientifically, LRH has been obtained in only very minute amounts and incompletely freed of impurities. Thousands, and sometimes hundreds of thousands, or hypothalamic fragments from as many animals are required to obtain minute quantities of the natural hormone and even then it is of doubtful total purity.

Working initially with 165,000 pig hypothalami, Schally, et al. (*Biochem. Biophys. Res. Commun.*, 43, (2), 393 (1971) ), ultimately obtained 830$\mu$ g of material which still was not completely pure, but which released both LH and FSH. This very limited quantity of material represented purification of over two million-fold.

It is clearly evident that the naturally occurring LRH derived from slaughter house tissue can hardly be obtained in sufficient quantity and purity to permit even the most exploratory diagnostic studies in medicine, and that obtaining LRH from this tissue for widespread practical use in medicine is impossible.

THE INVENTION

It has now been found that the decapeptide, L-pglutamyl-L-histidyl-L-tryptophanyl-L-seryl-L-tyrosyl-glycyl-L-leucyl-L-arginyl-L-prolyl-glycinamide, can be synthetically produced by utilizing starting materials which are both readily available or readily producible. The basic starting materials that can be utilized to synthesize the decapeptide of this invention are the following nine amino acids: N-carbobenzoxy pyroglutamic acid (Z-pGlu), t-butyloxycarbonyl histidine (t-Boc-His) or t-Butyloxycarbonyl-$^{im}$-benzyl histidine (t-Boc-$^{im}$Bzl-His), t-butyloxycarbonyltryptophan (t-Boc-Trp), t-butyloxycarbonyl-O-benzyl serine (t-Boc-Ser), t-butyloxycarbonyl-O-benzyl-tyrosin (t-Boc-O-Bzl-Tyr), t-butyloxycarbonylglycin (t-Boc-Gly), t-butyloxycarbonyl-leucine (t-Boc-Leu), t-butyloxycarbonyl-nitroarginine (t-Boc-$NO_2$Arg), t-butyloxycarbonyl-proline (t-Boc-Pro).

These nine amino acids can be used in their appropriate form for solid-phase synthesis of peptides. For example, t-Boc-glycine can be attached to chloromethylated or a nitrochloromethylated resin or other resin or carrier suitable for attachment of an amino acid. The initial amino acid-resin may also be an initial peptide-resin suitable for building up the remaining amino acids, one amino acid at a time, or by multiples of one amino acid in a sequential operation to ultimately yield decapeptide -$NH_2$.

The ultimate decapeptide bound to a resin or a carrier is removed with suitable acid cleavage to give decapeptide-OH, protected or unprotected, and appropriately converted into decapeptide-$NH_2$. Alternatively, the decapeptide-resin or carrier may be cleaved to give directly decapeptide-$NH_2$.

The decapeptide-$NH_2$ of this invention is very readily obtained in pure form by organic synthesis as described in greater detail hereinbelow. As such, the synthetic decapeptide-$NH_2$ readily lends itself to widespread medical practicality. The decapeptide-$NH_2$ is very useful to promote ovulation in mammalian species and in humans, it can overcome some causes of infertility and erratic fertility in women. In agriculture animals, it is useful to synchronize the fertility of animals and herds for breeding operations, and to induce fertility in rare and/or expensive animals, such as valuable breeding stock. It is useful to increase the number of newborn animals in a litter from sows, a matter of great economic importance, and to increase twinning in cows and ewes. Since the synthetic decapeptide-$NH_2$ performs the hormonal function of the natural hormone and can now be made abundantly available on an economical cost basis, it offers a great advantage over the natural LRH which, as indicated above, has been available only with great difficulty on a scientific basis and not at all on a practical basis for use in veterinary medicine, agriculture and/or human medicine.

The example given below is provided to exemplify the invention, and modifications of this example in terms of the single or multiple use of the amino acids, their protection, and deprotection, as well as the selection of the resin of the carrier for binding the amino acid or peptide prior to completion of the synthesis, the use of solvents, variations in concentrations, etc., are all considered in the scope of the invention.

EXAMPLE

The decapeptide pGlu-His-Trp-Ser-Tyr-Gly-Leu-Arg-Pro-Gly-$NH_2$ (I) having the full biological activity of the natural luteinizing hormone releasing hormone (LRH) is synthesized by a solid-phase peptide synthesis as follows:

t-Boc-Gly is attached to a chloromethylated resin (or nitrochloromethylated resin or other resin suitable for attachment of amino acids).

The reaction with the second amino acid, which is t-Boc-Pro is then carried out using the following sequence: (a) cleavage of the t-Boc group from the t-Boc-Gly resin (1 equivalent) using 25% trifluoroacetic acid (TFA) in methylene chloride ($CH_2Cl_2$) for 30 min.; (b) washing with $CH_2Cl_2$ 3 times; (c) neutralization of the TFA salt with 10% triethylamine ($Et_3N$) in $CH_2Cl_2$ for 15 min.; (d) washing with $CH_2Cl_2$, 3 times; (e) addition of t-Boc-Pro (3 equivalents) and mixing for 10 min; (f) addition of dicyclohexylcarbodiimide (DCI) (3 equivalents) in $CH_2Cl_2$ followed by a reaction period of 5 hours; (g) washing with $CH_2 Cl_2$ 3 times. Each washing period being about 5 minutes.

The cycle (a)-(g) is then repeated for the following eight amino acids, t-Boc-$NO_2$Arg, t-Boc-Leu, t-Boc-Gly, t-Boc-OBzl-Tyr, t-Boc-OBzl-Ser, t-Boc-Trp, t-Boc-His, and N-carbobenzoxy-pGlu (z-pGlu) or pGlu or as the last coupling reaction is pGlu-His or pGlu-His-Trp added to the octapeptide or heptapeptide, respectively, in order to obtain the desired decapeptide resin.

The pGlu-His-Trp-Ser-Tyr-Gly-Leu-Arg-Pro-Gly-resin is then suspended in MeOH saturated with ammonia at 0°C, and stirred in a tightly stoppered flask at room temperature for 48 hours. After filtration and evaporation of the solvent in vacuo, the residue is subjected to catalytic hydrogenation over Pd in order to remove the protective groups; i.e., carbobenzoxy from the pGlu-moiety, the nitro group from the arginine moiety, and the benzyl group from the serine and tyrosine moieties.

After purification using gel filtration and ion exchange chromatography, the decapeptide, pGlu-His-Trp-Ser-Tyr-Gly-Leu-Arg-Pro-Gly-$NH_2$ was found to be homogeneous in different chromatography systems showing positive color reactions with Pauly, Sakaguchi, Ehrlich and chlorine tolidine reagents, but revealed no color reaction with ninhydrin reagent. Acid hydrolysis showed the eight amino acids Glu (1), Gly (2), Pro (1), Leu (1), His (1), Tyr (1), Ser (1), Arg (1), and basic hydrolyses also showed the presence of Trp (1), the nearest integral of the amino acid ratios being indicated in parentheses.

One part of the decapeptide resin is cleaved using HF giving a free carboxy-terminal of the decapeptide (II). Another part is cleaved using $Et_3N$ (50 μ moles per mole peptide) in MeOH giving the protected decapeptide methyl ester (IV) which, after treatment with methanol saturated with ammonia and catalytic reduction, gives the decapeptide—$NH_2$ (I).

IV was subjected to catalytic hydrogenation giving the analog of I, having a carboxyl methyl ester (II).

DETAILED EXPERIMENTAL SECTION 5 g of t-Boc-glycine-resin = 3.5mM of glycine (0.7 mM of glycine/g of resin) was suspended in dioxane in the reaction vessel of a Beckman Model 990 Peptide Synthesizer. The following scheme was followed in order to introduce t-Boc-Pro on the resin.

a. Washing with dioxane (3 × 40 ml)
b. Prewash with 4 N HCl/dioxane (40 ml) for 1.5 min.
c. Deprotection with 4 N HCl/dioxane (40 ml) for 30 min.
d. Washing with dioxane (3 × 40 ml)
e. Washing with $CH_2Cl_2$ (3 × 40 ml)
f. Prewash with 10% $Et_3N/CH_2Cl_2$ (40 ml) 1.5 min.
g. Neutralization with 10% $Et_3N/CH_2Cl_2$ (40 ml) 10 Min.
h. Washing with $CH_2Cl_2$ (3 × 40 ml)
i. Addition of t-Boc-Pro (1.88 g, 8.75 mM) in $CH_2Cl_2$ (30 ml) and mixing for 10 min.
j. Addition of DCI in $CH_2Cl_2$ (1.80 g, 8.75 mM) followed by a reaction period of 4 hr.
k. Washing with $CH_2Cl_2$ (3 × 40 ml)

Thereafter scheme 1 was repeated for t-Boc-$NO_2$Arg, t-Boc-Leu, t-Boc-Gly, t-Boc-Tyr(Bzl), t-Boc-Ser(Bzl), t-Boc-Trp, t-Boc-His(Tos) and Z-pGlu using 8.25 mM of each protected amino acid. For t-Boc-$NO_2$Arg and t-Boc-Trp additional steps after (h) were inserted as follows:

i. Washing with DMF (3 × 40 ml)
j. Addition of t-Boc-$NO_2$Arg or t-Boc-Trp in DMF (30 ml) and mixing for 10 min.; followed by addition of DCI in $CH_2Cl_2$ (1.80 g, 8.75 mM).
k. After the reaction period of 4 hr. an addition wash with DMF (3 × 40 ml) was performed.

pGlu-His(Tos)Trp-Ser
(Bzl)-Tyr(Bzl)Gly-Leu-Arg($NO_2$)Pro-Gly-$NH_2$ (IV)

A part of the so obtained Z-pGlu-His(Tos)Trp-Ser(Bzl) Tyr(Bzl)-Gly-Leu-Arg($NO_2$)Pro-Gly-resin (2.0 g) was suspended in MeOH saturated with ammonia (20 ml) and stirred in a tightly stoppered flask at room temperature for 80 hr. After evaporation and purification, 540 mg of pGlu-His(Tos)-Trp-Ser(Bzl)-Tyr(Bzl)-Gly-Leu-Arg($NO_2$)Pro-Gly-$NH_2$ was obtained, showing one spot positive to Ehrlich and chlorine-tolidine reagents. Amino Acid analyses, Glu (1.01), His(Tos) (0.56, not corrected), Ser (0.88), Tyr (0.45, not corrected), Gly (2.00), Leu (1.00), $NO_2$-Arg (0.73, not corrected), Pro (0.92).

pGlu-His-Trp-Ser-Tyr-Gly-Leu-Arg-Pro-Gly-$NH_2$ (I)

The protected decapeptide amide IV (220 mg) was dissolved in a mixture of HF (10 ml) and anisole (1 ml) and a 15 fold excess of methionine was added for protection of the Trp moiety. After a reaction period of 45 min. at 0° the HF and anisole were evaporated and the residue was dissolved in 1% HOAc (50 ml) and lyophilized. This gave 410 mg of crude material, which was purified by countercurrent distribution (0.1% HOAc:n-BuOH:Pyridine (11:5:3 v/v/v)). The obtained product showed positive color reactions to Pauly, Ehrlich, Sakaguchi, and chlorine-tolidine reagents. The $R_f$ values of I were 0.40 in n-BuOH:EtOAc:HOAc:$H_2O$ (1:1:1:1) and 0.67 in $CHCl_3$:MeOH:concd. $NH_3$ (60:45:20). These $R_f$-values are identical to a sample of pGlu-His-Trp-Ser-Tyr-Gly-Leu-Arg-Pro-Gly-$NH_2$ prepared by a different route and described in copending application Ser. No. 210,122 filed Dec. 20, 1971, now abandoned. This compound increases the LH level 30 times at a dose of 25 ng. and at a dose of 50 ng a maximum increase of the LH level is obtained in the in vivo assay in rats.

pGlu-His-Trp-Ser-Tyr-Gly-Leu-Arg-Pro-Gly-OH (II)

The protected decapeptide-resin, pGlu-His(Tos)-Trp-Ser (Bzl)-Tyr(Bzl)-Gly-Leu-Arg($NO_2$) Pro-Gly-resin (1.5 g), was suspended in HF containing 10% anisole (10 ml). After a reaction period of 30 min. at 0° the solvent was evaporated in vacuo, and the residue was dissolved in 0.1% HOAc and lyophilized giving 492 mg crude material. A part of this was purified by thin layer chromatography giving a product positive to Pauly, Ehrlich, Sakaguchi, and chlorine-tolidine reagents. The $R_f$ values of II were 0.38 in n-BuOH:HOAc:EtOAc:$H_2O$ (1:1:1:1) and 0.63 ($CHCl_3$):MeOH:concd. $NH_3$ (60:45:20). Amino acid analyses: Glu (0.95), His (0.57), Ser (0.87), Tyr (1.14), Gly (2.00), Leu (0.95), Arg (0.89), Pro (1.05).

| | Biological Activity of II | |
|---|---|---|
| Dose Level | m$\mu$g LH/ml serum | |
| | before | after |
| 25 $\mu$g | 4.4 | 86.0 |
| 200 $\mu$g | 5.8 | 252.0 |
| | <4.0 | >285.0 |
| | 4.0 | >285.0 |

Of the three decapeptides pGlu-His-Trp-Ser-Tyr-Gly-Leu-Arg-Pro-Gly-$NH_2$ (I), pGlu-His-Trp-Ser-Tyr-Gly-Leu-Arg-Pro-Gly-OH (II), pGlu-His-Trp-Ser-Tyr-Gly-Leu-Arg-Pro-Gly-$OCH_3$ (III), I is most potent and releases LRH at doses of 1–25 ng.

The LRH assay was performed by the procedure of Ramirez and McCann (*Endocrinology* 73, 193 (1963)). Serum assays for LH were performed in duplicate by the double antibody radioimmuno assay of Niswender et al. (*Proc. Soc. Exp. Biol. Med.* 128, 807 (1968)) using antiovine LH serum and ovine LH-[131] I. The activity was determined by comparison of LH levels before and after injection of the peptide.

What is claimed:

1. A method for synthesizing the decapeptide, L-pglutamyl-L-histidyl-L-tryptophanyl-L-seryl-L-tyrosyl-glycyl-L-leucyl-L-arginyl-L-prolyl-glycinamide, comprising coupling, in appropriate protected forms, the amino acids, glycine, proline, arginine, leucine, glycine, tyrosine, serine, tryptophan, histidine, and pyroglutamic acid, said amino acids being sequentially coupled in their adjacently-named order and bound to a resin or carrier; and, releasing the protected decapeptide from said resin or carrier as the amide, the protected forms of said amino acids being provided by the protective groups, N-t-butyloxycarbonyl, $N^\alpha$ -t-butyloxycarbonyl-$N^G$-nitro, N-T-butyloxycarbonyl-O-benzyl, $N^\alpha$ -t-butyloxycarbonyl, $N^\alpha$ -t-butyloxycarbonyl-$N^{im}$-p-toluenesulfonyl, N-carbobenzoxy.

2. The method of claim 1 wherein the carboxyl terminal amino acid is initially attached in combination with at least one of the other adjacently-named amino acids.

* * * * *